US006773894B1

(12) United States Patent
Han et al.

(10) Patent No.: US 6,773,894 B1
(45) Date of Patent: Aug. 10, 2004

(54) ISOLATION AND EXTRACTION OF SUBCELLULARLY COMPARTMENTALIZED PROTEIN

(75) Inventors: Xiaoliang Han, San Francisco, CA (US); Fange Ni, Hayward, CA (US)

(73) Assignee: Biochain Institute, Inc., Hayward, CA (US)

( * ) Notice: Subject to any disclaimer, the term of this patent is extended or adjusted under 35 U.S.C. 154(b) by 0 days.

(21) Appl. No.: 09/575,496

(22) Filed: May 18, 2000

Related U.S. Application Data
(60) Provisional application No. 60/177,500, filed on Jan. 21, 2000.

(51) Int. Cl.[7] .................... G01N 33/567; G01N 33/543; C12N 9/96

(52) U.S. Cl. ............................ 435/7.2; 435/1.1; 435/6; 435/7.21; 435/91.1; 435/184; 435/188; 436/518; 436/536

(58) Field of Search .......................... 435/1.1, 6, 91.1, 435/91.2, 91.5, 91.52, 7.2, 7.21, 29, 40.5, 40.51, 288.3, 288.4, 5, 7.1, 188, 184, 810; 436/546, 172, 800, 809, 518, 536; 424/8, 12; 23/230 B

(56) References Cited

U.S. PATENT DOCUMENTS

| | | | | |
|---|---|---|---|---|
| 4,281,061 A | * | 7/1981 | Zuk et al. ........................ | 435/7 |
| 4,444,879 A | * | 4/1984 | Foster et al. .................... | 435/7 |
| 4,776,853 A | * | 10/1988 | Klement et al. .............. | 8/94.11 |
| 4,885,236 A | * | 12/1989 | Penman et al. ................. | 435/6 |
| 5,550,019 A | * | 8/1996 | Reed .............................. | 435/6 |
| 5,989,835 A | * | 11/1999 | Dunlay et al. ............... | 435/7.2 |
| 6,093,543 A | * | 7/2000 | Coll et al. ...................... | 435/6 |

OTHER PUBLICATIONS

Maltese et al., "Isoprenylated proteins in cultured cells: subcellular distribution and changes related to altered morphology and growth arrest induced by mevalonate deprivation." Journal of Cellular Physiology, 1987, 133(3), pp. 471–481.*
Hirano et al., "A new synthetic protease inhibitor, E–3123, reduces organelle fragility of acinar cells in rat caerulein pancreatitis.", Nippon Geka Hokan, Archiv Fur Japanische Chirurgie, Nov. 1, 1991, 60(6), pp. 406–414.Abstrcat Only.*
Tani et al., "Aqueous micellar two–phase systems for protein separation." Analytical Science, 1998, 14(5), pp. 875–888.*
Wild et al., "Influence of calcium and magnesium containg fixatives of the tultrstructure of parathroids.", Micron and Microscopica Acta, 1987, 18(4), pp. 259–271. Abstract Only.*
Kelly et al. "Subcellular localization of the 52,000 molecular weight major postsynaptic density protein." Brain Research, Feb. 11, 1982, vol. 233., No. 2., pp. 265–286, Abstract Only.*

(List continued on next page.)

Primary Examiner—Long V. Le
Assistant Examiner—Lisa V Cook
(74) Attorney, Agent, or Firm—Pacific Law Group LLP; C. P. Chang

(57) ABSTRACT

The invention provides methods of separating and isolating protein from at least three subcellular compartments of a single biological sample in a single container. Methods are also provided for determining the subcellular compartmentalization of proteins of interest in a biological sample. Furthermore, methods are provided for fingerprinting a biological sample, as well as identifying a sample type, a cancerous tissue or a developmental stage of a tissue sample. Kits for separating and isolating subcellularly compartmentalized proteins in a biological sample are also provided.

10 Claims, 16 Drawing Sheets

OTHER PUBLICATIONS

Carr et al., "Distribution of thyroid hormone–responsive translated products in rat liver polysome and postribosomal ribonucleoprotein polpulations." Endocrinology, 1984, vol. 115., No. 5., pp. 1737–1745. Abstract Only.*

Welshons et al., "Subcllular compartmentalization of MCF–7 estrogen receptor synthesis and degradtion." Molecular and Cellular Endocrinology, 1993, vol. 94., No. 2., pp. 183–194. Abstract Only.*

Kim et al., "Subclass–specific nuclear localization of a novel CD4 silencer binding factor.", Journal of Experimental Medicine, Jul. 19, 1999, vol. 190, No. 2., pp. 281–291. Abstract Only.*

Martinez–Garcia, et al., "A simple, rapid and quantitative methods for preparing Arabidopsis protein extracts for immunoblot analysis," *Plant J* 20(2):251–257 (1999).

Handen, et al., "An improved method for southwestern blotting," *Front Biosci* 2:c9–c11 (1997), Fontier in Biossience.

Wang, et al., "Total protein extraction from cultured cells for use in electrophoresis and western blotting," *Biotechniques* 20(4):662–668 (1996) Apr.

Horvath, et al., "Rapid protein extraction from *Saccharomyces cerevisiae*," *Yeast* 10(10):1305–1310 (1994).

Collet, et al., "Optimizing a method of protein extraction for two–dimensional electrophoretic separation of proteins from planarians (Platyhelminthes, Turbellaria)", *Electrophoresis* 14(10):1054–1059 (1993).

Jackson et al., "Poly Peptides of the nuclear envelope.", Biochemistry, 1976, vol. 15, No. 25, pp.5641–5651. Abstrcat Only.*

* cited by examiner

Panel A
Colon normal
T C N M

Panel B
Breast tumor
T C N M

Colon — Tumor T C N M  Metastasis T C N M

Breast — Tumor T C N M  Metastasis T C N M

ISOLATION AND EXTRACTION OF SUBCELLULARLY COMPARTMENTALIZED PROTEIN

This application is a continuation of provisional application No. 60/177,500 filed Jan. 21, 2000

FIELD OF THE INVENTION

The invention is directed to methods of separating and isolating protein from biological samples comprising cells. More specifically, the invention is directed to methods of separating and extracting protein from different subcellular compartments of cells in a biological sample. The invention is also directed to a kit for isolating and extracting protein from different subcellular compartments of cells in a biological sample.

BACKGROUND OF THE INVENTION

Protein is a basic component of cells and the subject of a vast area of research. Location of a protein within a cell is related to the function of the protein. For example, a protein involved in intracellular signal transduction would be expected to be found in the cytoplasmic compartment of a cell. A transcription factor protein would be found in the nuclear compartment of a cell, while a receptor would be found in the cell membrane. Therefore, isolation of a protein from a specific compartment of a cell (e.g., the cytoplasmic compartment, the nuclear compartment or the cell membrane compartment) is useful for studying the protein's function. Determination of cellular compartmental localization is also a standard technique in the study of Functional Genomics.

Many assays are used in the study of protein function. These include Western Blot, immunoprecipitation, receptor binding assays, protein-DNA and protein-mRNA binding assays, transcription assays, signal transduction assays, enzyme activity assays, phosphorylation and dephosphorylation analysis, etc. These assays generally require that the structure and activity of a protein of interest be maintained. The methods used to isolate and extract protein from its source should be compatible with the procedures to which the protein will subsequently be subjected. Ideally, the methods of isolation and extraction used should maintain the primary (sequence), secondary (folding) and tertiary (subunits) structure of the protein. This is best achieved with a minimum of manipulation of the protein during the isolation and extraction process.

In addition to preserving structure and activity of protein, several other parameters are also important in the choice of a protein isolation and extraction process. These include recovery rate, quickness and ease of use, and scalability. Of further importance is maintenance of the ratio of protein extracted from different subcellular compartments of a sample for gene expression analysis. The current methods of isolation and extraction of protein from a biological sample include density gradient centrifugation, ultra-centrifugation, concentration, dialysis, chromatography, precipitation, electrophoresis and selective banding. Unfortunately, each of these methods has one or more shortcomings with regard to the parameters listed above. Effective methods of extracting nuclear protein are available, but they generally exclude isolation and extraction of proteins from the cytoplasmic and membrane compartments of a cell.

Due to the broad interest in protein isolated from specific subcellular compartments and the importance of the various considerations described above for the means of such protein isolation and extraction, there is a need for a simple and effective method of isolating and extracting protein from different subcellular compartments of biological samples. A method that maintains protein structure and function, as well as the natural ratio of proteins, from different subcellular compartments can be applied to many different types of investigation of protein function. Accordingly, the present invention provides quick, simple and widely applicable methods for the isolation and extraction of protein from different subcellular compartments of biological samples.

SUMMARY OF THE INVENTION

The present invention provides methods of separating and isolating protein from at least three subcellular compartments of a single biological sample. The invention further applies the characterization of the subcellular distribution of proteins for fingerprinting and identifying different types of biological samples.

In one aspect, the invention provides a method of separating and isolating protein from at least three different subcellular compartments of a biological sample. In a preferred embodiment, the sample is homogenized and incubated in a cytoplasmic protein extraction solution, then centrifuged, and the supernatant containing the cytoplasmic protein is extracted. The pellet is then resuspended in a nuclear protein extraction solution, incubated, centrifuged, and the nuclear protein is extracted. The pellet is then resuspended, incubated in a membrane protein extraction solution, incubated, centrifuged, and the membrane protein is extracted. Preferably, the cytoplasmic protein extraction solution is a low osmotic solution, the nuclear protein extraction solution is a high osmotic solution, and the membrane protein extraction solution is a low osmotic solution containing a surfactant. In a preferred embodiment, the nuclear protein extraction solution contains at least one DNase. Preferably, each of the solutions contain protease inhibitors. Preferably, all of the incubation and centrifugation steps are performed in the same container, and preferably sequentially so as to be considered one procedure. In a preferred embodiment, the amounts of protein in each protein-containing supernatant is measured, whereby the total protein per weight of sample and the relative distribution of protein in each subcellular compartment is determined. The biological sample may be of organisms, tissue or cells, as long as the sample contains cells.

In another aspect of the invention, provided herein are methods of determining the subcellular compartmentalization of one or more proteins of interest in a biological sample. The protein from at least three subcellular compartments is separated and isolated, as described above. The presence of the protein(s) of interest in the protein isolated from one or more of the subcellular compartments is then determined. The determination of the presence of the protein (s) of interest may be by any of the many methods known in the art for identifying a specific protein.

The invention also provides methods of fingerprinting a biological sample. Protein from at least three subcellular compartments of the sample is separated and isolated, as described above. The pattern of protein present in the protein isolated from each subcellular compartment is then determined and the patterns are used to fingerprint the sample.

In a further aspect of the invention, methods of identifying the type of a biological sample are provided. Protein from subcellular compartments of the sample are separated and isolated as above, as is the pattern of protein present in the protein isolated from each of the subcellular compartments.

Alternatively, these patterns are compared to patterns of protein from the same subcellular compartments in biological samples of known type.

Also provided are methods of identifying cancerous tissue or cells. Protein from subcellular compartments of the sample are separated and isolated as above, as is the pattern of protein present in the protein isolated from each of the subcellular compartments. Alternatively, these patterns are compared to patterns of protein from the same subcellular compartments in known normal and/or known cancerous tissue of the same type as the sample. The cancerous tissue or cells may be metastatic or of a tumor.

In a further aspect of the invention, provided herein are methods of identifying the developmental stage of a tissue sample. Protein from subcellular compartments of the sample are separated and isolated as above, as is the pattern of protein present in the protein isolated from each of the subcellular compartments. Alternatively, these patterns are compared to patterns of protein from the same subcellular compartments in tissue of the same type and of known developmental stage.

The invention also provides a kit for separating and isolating subcellularly compartmentalized proteins from a biological sample. The kit contains a cytoplasmic extraction solution, a nuclear protein extraction solution and a membrane protein extraction solution. The kit may also contain means for separating and isolating protein from each of the cytoplasmic compartment, the nuclear compartment and the membrane compartment of the biological sample.

DETAILED DESCRIPTION OF THE INVENTION

Figure 1:
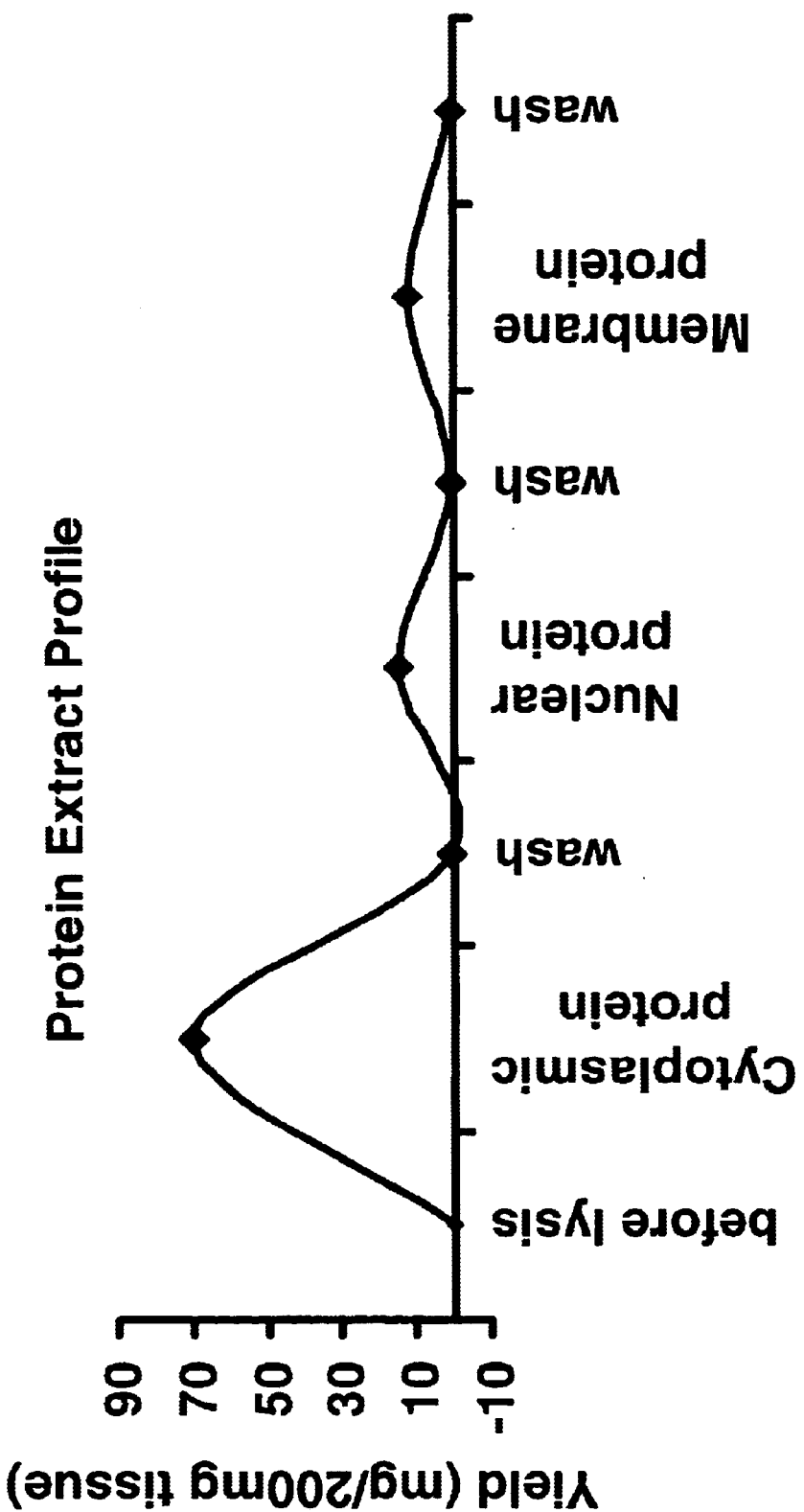
FIG. 1 shows the yield of protein extracted from three different subcellular compartments of a sample of human liver tissue and the washes between each extraction.

The present invention is directed to methods for the isolation and extraction of protein from subcellular compartments of a biological sample comprising cells. The invention provides for effective isolation and extraction of protein from the cytoplasmic, nuclear and membrane compartments of the cells in a biological sample. The methods are simple to perform, the isolation and extraction for each compartment taking place from the same sample in the same vessel. The methods minimize the manipulation of the sample. And, the methods may be applied to a vast number of applications including gene and protein function analyses, tissue type fingerprinting and distinguishing tumor tissue from normal tissue.

The present invention provides a method for separation and isolation of compartmentalized proteins from a sample of organisms, tissue, or cells. Herein said sample is a single source for the protein extracted from each subcellular compartment. From this single sample, cytoplasmic protein, nuclear protein or membrane protein are separated and extracted as three protein isolates. Therefore, the ratio of protein between the three cellular compartments is kept the same as the natural ratio in whole tissues or cells, which is valuable for the study of gene expression. This is an improvement over isolation of protein from the three cellular compartments using three separate samples. Recovery rate of isolated proteins is higher than other methods because all processes are performed in the same container and the number of steps involved is minimized.

The present invention also provides methods for separation and isolation of protein from three subcellular compartments from a sample of organisms, tissue, or cells with optimized preservation of structure and activity of proteins isolated. The methods are applicable to primary tissue, primary cell suspensions or cultured cells. The sample can be from virtually any species of life having cells with a cell membrane and a nuclear membrane. The method can take less than an hour to perform and is very easy to scale up or down.

In addition, the methods of the present invention are easy to perform. There are only three sequential steps of incubation, centrifugation and extraction. The present invention does not use demanding processes such as density gradient centrifugation, ultra-centrifugation, concentration, dialysis, chromatography, precipitation, electrophoresis, or selective banding which waste large amounts of protein. The present methods are further simplified as the invention also provides an easy to use kit for separation and isolation of protein from a sample of organisms, tissue, or cells.

Accordingly, the present invention provides methods and compositions for isolation and extraction of subcellularly compartmentalized protein from a biological sample comprising cells. In general, the invention entails isolation and extraction of cytoplasmic protein from the sample using a cytoplasmic protein extraction solution, followed by isolation and extraction of nuclear protein using a nuclear protein extraction solution, followed by isolation and extraction of membrane protein from the sample using a membrane protein extraction solution. At each extraction, the protein from the given subcellular compartment (e.g., cytoplasm, nucleus or membrane) is removed from the rest of the sample, providing at least three separate pools of protein, as is more fully described below. It is understood that the methods may be applied to extract protein from fewer than three subcellular compartments.

The invention provides methods for separating and isolating protein in a biological sample. By "separating" herein is meant physically dividing a subpool of protein from an initial larger pool. By "isolating" herein is meant providing a subpool of protein that is essentially free of contamination from protein from other subpools of an initial larger pool of protein. It is understood that isolating protein inevitably involves separating protein, in the context of the invention.

The methods provided herein involve separating and isolating protein in a biological sample comprising cells. By "protein" herein is meant at least two covalently attached amino acids, including proteins, polypeptides, oligopeptides and peptides. The protein is preferably produced in the biological sample. The proteins may be naturally occurring or produced in the biological sample as a result of recombinant manipulation. Production of the protein may be through transcription and translation of genes within the genome of cells in the biological samples, or through expression of plasmids or other nucleic acids independent from a cell's genome.

By "biological sample comprising cells" herein is meant any organisms, cell cultures, organs, tissues or parts thereof having cells as a component. Preferably, the biological sample comprising cells consists essentially of cells. Preferably the cells of the biological sample are intact prior to initiation of the present methods. Preferably, the cells of the biological sample comprise a cytoplasm, a nucleus and a membrane structure.

The biological sample may be any organisms, organs or samples of organs or cells. Preferred organisms include eukaryotes, preferably yeast. Organs may be from any multicellular organism having organs. Preferably, the organ is from a mammal, preferably a human. Preferred organs include heart, kidney, liver, trachea, lung, esophagus, stomach, intestine including small intestine and colon, rectum, spleen, ovary, uterus including cervix, placenta, breast, pancreas, testes, penis, brain, spinal cord, eye, skin, mucous membrane, gland including salivary gland and thymus, vasculature including vein and artery, or blood including leukocytes. Cells may be any cells including samples from an organism, primary cell cultures and cell lines.

In a preferred embodiment, the invention provides a method of separating and isolating protein from at least three different subcellular compartments of a biological sample comprising cells. By "subcellular compartment" herein is meant an identifiable component of a cell. Identifiable components of a cell which may be classified as subcellular compartments include the cytoplasm, the nucleus, and membrane structures including internal and external membranes, referred to herein as the "cytoplasmic compartment", the "nuclear compartment" and the "membrane compartment", respectively.

By "subcellularly compartmentalized" herein is meant localized predominantly within one or more subcellular compartments of a cell, to the exclusion of one or more other subcellular compartments of a cell. Therefore, protein confined predominantly to the cytoplasm of a cell is referred to herein as "cytoplasmic protein". Likewise, protein confined predominantly to inside the nucleus is referred to herein as "nuclear protein". And, protein incorporated into or otherwise structurally associated with membrane structures is referred to herein as "membrane protein". It is understood that other subcellular compartments, which may be subdivisions of the cytoplasmic, nuclear and membrane compartments described above, may also be identified.

In one aspect of the invention, as a first step in the method of the present invention, cytoplasmic protein is isolated and extracted from a biological sample comprising cells. In a preferred embodiment organisms, tissue or cells are homogenized, for example by mill, tissue grinder, blender, mortars and pestles, ultra-sonic, vortex or homogenizers, in a cytoplasmic protein extraction solution to generate a cytoplasmic protein suspension. The cytoplasmic protein suspension is then allowed to incubate. In a preferred embodiment, the cytoplasmic protein suspension is incubated at about 4° C. for about 5 to 30 minutes. The cytoplasmic protein solution is then centrifuged. In a preferred embodiment, said cytoplasmic protein suspension is centrifuged at 14000 rpm for about 10 minutes. The supernatant is then taken as cytoplasmic protein, leaving the nuclear and membrane pellet in the original container.

By "cytoplasmic protein extraction solution" herein is meant a low osmotic solution (i.e., would create low osmotic pressure against a homogenate of cells) in which cytoplasmic protein in homogenized cells will suspend under centrifugation, to the exclusion of the nuclear compartment and protein therein (nuclear protein) and the membrane compartment and protein therein (membrane protein).

In a preferred embodiment, the cytoplasmic protein extraction solution comprises a Solution C. Solution C comprises 2–3 mM HEPES-KOH, pH 7.9, 0.5–3 mM $MgCl_2$, 2–30 mM KCl, 20–500 mM Sucrose, 2–30% Glycerol, 0.2–3 mM EDTA, and 0.5–3 mM Sodium Orthovanadate. Most preferably, Solution C comprises 10 mM HEPES-KOH, pH 7.9, 1.5 mM $MgCl_2$, 10 mM KCl, 200 mM Sucrose, 10% Glycerol, 1 mM EDTA, and 1.5 mM Sodium Orthovanadate. The skilled artisan will appreciate that solutions having characteristics similar to Solution C, thus satisfying the criteria for a cytoplasmic protein extraction solution, are readily obtained without undue experimentation.

The pellet containing the nuclear and membrane protein is then resuspended in a nuclear protein extraction solution. This suspension is mixed to generate a nuclear protein suspension. The nuclear protein suspension is then allowed to incubate. In a preferred embodiment, said nuclear protein suspension is incubated at 4° C. for about 5 to 30 minutes. The suspension is then centrifuged. In a preferred embodiment, said nuclear protein suspension is centrifuged at 14000 rpm for about 10 minutes. The supernatant is then taken as nuclear protein and the membrane pellet is left in the same container.

By "nuclear protein extraction solution" herein is meant a high osmotic solution (i.e., would create high osmotic pressure against a homogenate of cells) in which nuclear protein will suspend under centrifugation to the exclusion of the membrane compartment and protein therein (membrane protein).

In a preferred embodiment, the nuclear protein extraction solution comprises a Solution N. Solution N comprises 5–50 mM HEPES-KOH, pH7.9, 5–35% Glycerol, 100–600 mM NaCl, 0.5–3 mM $MgCl_2$, and 0.1–3 mM EDTA. Most preferably Solution N comprises 20 mM HEPES-KOH, pH7.9, 25% Glycerol, 420 mM NaCl, 1.5 mM $MgCl_2$, and 0.2 mM EDTA. The skilled artisan will appreciate that solutions having characteristics similar to Solution N, thus satisfying the criteria for a nuclear protein extraction solution, are readily obtained without undue experimentation.

In a preferred embodiment, the nuclear protein extraction solution comprises a DNase. This embodiment increases the yield of protein in the nuclear protein extraction step of the method under circumstances in which DNA in the sample is "sticking" to the protein.

The membrane pellet is then mixed with membrane protein extract solution and resuspended to generate a membrane protein suspension. In a preferred embodiment, said membrane protein suspension is incubated at 4° C. for about 5 to 30 minutes. The membrane protein suspension is then centrifuged. In a preferred embodiment, said membrane protein suspension is centrifuged at 14000 rpm for about 10 minutes. The supernatant is taken as membrane protein.

By "membrane protein extraction solution" herein is meant a low osmotic solution comprising a surfactant in which membrane protein will suspend under centrifugation to the exclusion of other non-protein components of the membrane compartment.

In a preferred embodiment, the membrane protein extraction solution comprises Solution TM. Solution TM comprises 2–30 mM HEPES-KOH, pH 7.9, 0.5–3 mM $MgCl_2$, 2–30 mM KCl, 20–500 mM Sucrose, 2–30% Glycerol, 0.2–3 mM EDTA, 0.2–5% NP-40, 0.1–3% Sodium Deoxycholate, and 0.5–3 mM Sodium Orthovanadate. Most preferably, Solution TM comprises 10 mM HEPES-KOH, pH 7.9, 1.5 mM $MgCl_2$, 10 mM KCl, 200 mM Sucrose, 10% Glycerol, 1 mM EDTA, 1% NP-40, 0.5% Sodium Deoxycholate, and 1.5 mM Sodium Orthovanadate. The skilled artisan will appreciate that solutions having characteristics similar to Solution TM, thus satisfying the criteria for a membrane protein extraction solution, are readily obtained without undue experimentation.

It is understood by those in the art that the extraction solutions can comprise additional components, for example protease inhibitors. In a preferred embodiment, each of the extraction solutions comprise one or more protease inhibitors. In one embodiment, each extraction solution comprises a solution PI. Preferably, Solution PI comprises Aprotinin, Antipain, Bestatin, E-64, Leupeptin, and Pepstatin A. Preferably Solution PI (50×) will contain 25–250 μg/ml Aprotinin, 10–150 μg/ml Antipain, 10–150 μg/ml Bestatin, 5–100 μg/ml E-64, 25–250 μg/ml Leupeptin, and 5–100 μg/ml Pepstatin A. Most preferably, Solution PI (50×) will contain 100 μg/ml Aprotinin, 50 μg/ml Antipain, 50 μ/ml Bestatin, 25 μg/ml E-64, 100 μg/ml Leupeptin, and 25 μg/ml Pepstatin A. Solution PI is preferably mixed into each of the extraction solutions at a ratio of about 48:1 Solution C, N or TM to Solution PI.

As will be understood in the art, each extraction solution may comprise additional components. In a preferred embodiment, each extraction solution comprises a Solution CI. Preferably, Solution CI comprises DTT, AEBSF, and PMSF. Preferably, Solution CI (50×) will contain 5–100 mM DTT, 2.5–50 mM AEBSF, and 5–100 mM PMSF. Most preferably, Solution CI (50×) will contain 25 mM DTT, 10 mM AEBSF, and 2 mM PMSF. Solution CI is preferably mixed into each extraction solution at a ratio of about 48:1 Solution C, N or TM to Solution CI.

It is understood in the art that additional steps, such as washes, may be added to optimize the presently described invention without deviating from the invention itself.

There are some precautions one should pay attention to during separation or isolation of protein by the present methods. Homogenization of sample in cytoplasmic protein extraction solution should be kept to a minimum to prevent breakage of nuclear membrane. Dnase can be added to the suspensions, should DNA prevent isolation of nuclear or membrane proteins. The concentration of surfactant can be adjusted to maximize membrane protein isolation or preservation of structure or activity of protein isolated. The volume of extraction solution should be adjusted to prevent saturation or over-dilution.

The present invention also provides a kit to be used for the separation and isolation of compartmentalized proteins. The kit comprises a cytoplasmic protein extraction solution, a nuclear protein extraction solution, and a membrane protein extraction. The kit may also provide means to combine the different solutions and to extract compartmentalized protein or total protein from a sample of organisms, tissue or cells.

Appropriate separation or isolation of compartmentalized proteins from a sample of organisms, tissue, or cells can be verified by yield of protein from each compartment, protein band pattern analysis of protein from each compartment, Western analysis of known compartment-specific proteins, or DNA location analysis to confirm proper separation of nuclear compartment from other compartments.

In a preferred embodiment, the amount (yield) of protein in each extraction of the sample is determined. Assays are commercially available for determining the amount of protein in a solution (e.g., by determining concentration, as exemplified below). This determination will reveal not only the ratio of protein in each of the subcellular compartments, but also the total amount of protein in the sample, which may be expressed as a percentage of the total wet weight of the sample.

The present invention has applicability in a variety of analyses, such as gene function analysis (Functional Genomics), protein function analysis (Proteomics), differentiation of normal tissue types (Fingerprinting), identification of developmental stages from fetus to adults, differentiation of normal tissue from tumor tissues, comparison of primary tumor tissue and metastasis tumor tissue, etc. These analyses are based on the location of specific proteins in a cell compartment, amount of protein in each cell compartment or a combination of both.

Location of protein in cell compartments and amount of protein in cell compartments are valuable information for gene function analysis. For instance, an antibody generated by an unknown gene product may bind to a protein on the cell membrane, which indicates that this unknown gene may encode a receptor. This assay plays an important role in Functional Genomics. Changes of one protein band pattern among subcellular compartments, when related or correlated to a change in cell function or activity, indicates the function of this protein, which is the focus of Proteomics.

Different types of normal tissues, such as liver and lung, show different protein band patterns among subcellular compartments, which can serve as a fingerprint for a particular tissue. The fact that protein band patterns are different in fetus from the protein patterns in adult provides clues to identifying those proteins that play a significant role in development.

Accordingly, the present invention provides methods for determining the subcellular compartmentalization of one or more proteins of interest in a biological sample comprising cells. By "protein of interest" herein is meant any identifiable protein under conscious consideration. The method comprises separating and isolating protein from different subcellular compartments, as described above, and determining the presence of the protein(s) of interest among the protein from each of the subcellular compartments.

It will be appreciated by those skilled in the art that any biological sample that may be used in the methods described above may be used in any of the other methods described herein. Therefore, the subcellular compartmentalization of one or more proteins of interest may be determined for any biological sample comprising cells, including organisms, cell cultures, organs and tissues and parts of any thereof.

Determination of the presence of one or more proteins of interest in the instant embodiment may be made by any of the numerous methods known in the art. Such determination methods include, but are not limited to, gel band pattern analysis, direct or indirect antibody staining, including Western blot analysis and ELISA, enzyme activity analysis, ligand binding analysis and receptor binding analysis.

The present invention can be employed to the analysis of protein differential display. For instance, identification of proteins which have changed compartmental status between normal tissues and tumor tissues provides direction to focus on these suspicious proteins to develop diagnostic or treatment tools. This principle can be employed to many other similar applications. Based on the fact that the different tissues have their own "finger prints", and the protein band patterns of normal tissue and tumor tissue are different, the protein pattern database can be established for diagnostic application. With a set of protein "finger prints", one can identify different tissues, diagnose tumor or metastasis, and design treatment programs.

Accordingly, the invention provides a method of fingerprinting a biological sample comprising cells. By "fingerprinting", "determining a fingerprint" and grammatical equivalents thereof is meant determining the differential protein content of subcellular compartments in the sample. Such determining includes both total protein content, as described above, as well as the pattern of protein present. By "pattern of protein present" herein is meant the individual types of protein and/or the presence and relative amounts of proteins of different size/molecular weight, migration rate in a gradient or gel, binding affinity and/or enzyme activity in a subcellular compartment of a biological sample.

The method of fingerprinting generally involves separating and isolating protein from different subcellular compartments of a biological sample comprising cells, as described above, then determining the pattern of protein present in each subcellular compartment. In a preferred embodiment, the pattern of protein present is determined by comparing the distribution of bands of protein from each of the subcellular compartments separated in an SDS gel.

In a preferred embodiment, the method of fingerprinting involves determining the pattern of protein in at least three different subcellular compartments of a biological sample comprising cells. In a preferred embodiment, the pattern of protein present is determined from at least the cytoplasmic compartment, the nuclear compartment and the membrane compartment of a biological sample.

The method of fingerprinting described above, as a preferred embodiment of the invention, has many useful applications. In one embodiment, the invention provides a method of identifying the type of a biological sample comprising cells. By "type of biological sample" herein means the source of the sample, such as a particular organism, a particular tissue or organ, a particular cell line, etc. The method generally involves separating and isolating protein of different subcellular compartments and determining the pattern of protein present in each. The fingerprint of the sample is used to determine its type. Alternatively, the pattern of protein for each subcellular compartment is compared to the patterns of known tissue type, the known patterns providing a reference whereby the type of the biological sample is determined.

In a preferred embodiment, the method involves separating and isolating protein from at least three subcellular compartments. In a preferred embodiment, the pattern of protein present is determined from at least the cytoplasmic compartment, the nuclear compartment and the membrane compartment of a biological sample. Preferably, the patterns are compared to patterns of protein from the same subcellular compartments of known biological sample types.

The present invention has been used to discover that tumors show different protein band patterns from those of the same type of normal tissue. This means that tumors contain different protein populations and/or different subcellular compartmentalization of protein from normal tissues, even though the tissue type is the same. On the other hand, primary tumor shows similar protein band patterns as those of metastatic tumor originating from the same primary tumor. Furthermore, metastatic tumor tissues from different primary tumors show similar protein band patterns to each other, and different tumors originating from different types of tissue show relatively similar protein band patterns, which indicates that different tumors contain similar protein populations and/or have similar subcellular compartmentalization of protein even though these tumors originated from different types of normal tissue. Therefore, application of the present invention shows that all of the tumors originating from different types of normal tissue contain relatively similar protein populations. This coincides with the fact that tumors are in low differentiated status, thus containing a smaller variety of proteins.

Accordingly, the invention provides a method of identifying cancerous cells or tissue. By "cancerous tissue" herein is meant tissue containing cancer cells. The method generally involves separating and isolating protein from different subcellular compartments from a cell or tissue sample of an individual and determining the pattern of protein contained in each compartment. Alternatively, the pattern of protein in each subcellular compartment of the cell or tissue sample is compared to known patterns from normal and/or cancerous cells or tissue of the same type as the sample. The cancer cells may be of a tumor or metastatic. In a preferred embodiment, the method involves separating and isolating protein from at least three subcellular compartments. In a preferred embodiment, the pattern of protein present is determined from at least the cytoplasmic compartment, the nuclear compartment and the membrane compartment of a biological sample.

In another embodiment, the invention provides a method of identifying the developmental stage of a tissue sample. By "developmental stage" herein is meant the stage of development from an embryo to adult from which the tissue sample is taken. Developmental staging is a standard practice in the art, and any method may be used, as long as it has been standardized. The method generally involves separating and isolating protein from different subcellular compartments from tissue sample of an individual and determining the pattern of protein contained in each compartment. Alternatively, the pattern of protein in each subcellular compartment of the tissue sample is compared to patterns from the same subcellular compartments of the same tissue of known developmental stage. In a preferred embodiment, the method involves separating and isolating protein from at least three subcellular compartments. In a preferred embodiment, the pattern of protein present is determined from at least the cytoplasmic compartment, the nuclear compartment and the membrane compartment of a biological sample.

The invention also provides a kit for separating and isolating subcellularly compartmentalized proteins. The kit generally contains at least a cytoplasmic protein extraction solution, a nuclear protein extraction solution and a membrane protein extraction solution. In addition the kit may contain equipment and supplies useful to perform the separation and isolation of the protein from each subcellular compartment.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Materials and Methods

Preparation of Solutions

Solution C contains 10 mM HEPES-KOH, pH 7.9 (Sigma, P.O. Box 14508, St. Louis, Mo. 63178 USA, Cat. #H0527), 1.5 mM $MgCl_2$ (Sigma, Cat. #M8266), 10 mM KCl (Sigma, Cat. #P4504), 200 mM Sucrose (Sigma, Cat. #S9378), 10% Glycerol (Sigma, Cat. #G7893), 1 mM EDTA (Sigma, Cat. #E9884), and 1.5 mM Sodium Orthovanadate (Sigma, Cat. #S6508).

Solution N contains 20 mM HEPES-KOH, pH7.9 (Sigma, Cat. #H0527), 25% Glycerol (Sigma, Cat. #G7893), 420 mM NaCl (Sigma, Cat. #S9888), 1.5 mM $MgCl_2$ (Sigma, Cat. #M8266), and 0.2 mM EDTA (Sigma, Cat. #E9884).

Solution TM contains 10 mM HEPES-KOH, pH 7.9 (Sigma, Cat. #H0527), 1.5 mM $MgCl_2$ (Sigma, Cat. #M8266), 10 mM KCl (Sigma, Cat. #P4504), 200 mM Sucrose (Sigma, Cat. #S9378), 10% Glycerol (Sigma, Cat. #G7893), 1 mM EDTA (Sigma, Cat. #E9884), 1% NP-40 (Sigma, Cat. #NP-40), 0.5% Sodium Deoxycholate (Sigma, Cat. #D6750), and 1.5 mM Sodium Orthovanadate (Sigma, Cat. #S6508).

Solution PI (50×) contains 100 μg/ml Aprotinin (Sigma, Cat. #A1153), 50 μg/ml Antipain (Sigma, Cat. #A6191), 50 μg/ml Bestatin (Sigma, Cat. #B8385), 25 μg/ml E-64 (Sigma, Cat. #E3132), 100 μg/ml Leupeptin (Sigma, Cat. #L0649), and 25 μg/ml Pepstatin A (Sigma, Cat. #P4265).

Solution CI (50×) contains 25 mM DTT (Sigma, Cat. #D5545), 10 mM AEBSF (Sigma, Cat. #A8456), and 20 mM PMSF (Sigma, Cat. #P7626).

TNT Blocking buffer contains 10 mM Tris-HCl, pH 7.9 (Sigma, Cat. #T1503), 150 mM NaCl (Sigma, Cat. #S9888), 0.1% Tween-20 (Sigma, Cat. #P1379), and 2.0% BSA (Sigma, Cat. #A7906).

Transfer Buffer contains 25 mM Tris-base (Sigma, Cat. #T1503), 192 mM Glycine (Sigma, Cat. #G7126), and 20% Methanol (Sigma, Cat. #M3641).

Human Embryo Kidney 1 (HEK1) cells were used (Catalog Number CRL-1573, ATTC, 12301 Parklawn Drive, Rockville, Md. 20852-1776). Human peripheral blood leukocytes were collected from Pacific Blood Center, San Francisco, Calif. 94120. Other materials and reagents were provided by BioChain Inc.(Hayward, Calif. 94545).

Extraction of Compartmentalized Protein or Total Protein

A. Extraction of Cytoplasmic, Nuclear and Membrane Protein

Frozen tissues or fresh cell pellets were weighed. 200 mg of each tissue or cell pellet was homogenized with a hand-held homogenizer in ice-cold 480 μl Solution C, 10 μl Solution PI (50×) and 10 μl Solution CI (50×) (48:1:1). The resultant slurry was incubated at 4° C. for 10 minutes and centrifuged at 14000 rpm for 10 minutes using a microcentrifuge. The supernatant was transferred into a fresh Eppendorf tube—this is cytoplasmic protein. The pellet was washed twice with 300 μl Solution C prior to lysis in ice-cold 192 μL Solution N, 4 μl Solution PI (50×) and 4 μl Solution CI (50×) (48:1:1). The suspension then was incubated at 4° C. for 10 minutes and the supernatant, after spin, was transferred into a second Eppendorf tube—this is nuclear protein. The pellet again was washed by 300 μl Solution C before extracting membrane proteins. Then ice-cold 192 μl buffer TM, 4 μl Solution PI (50×) and 4 μl Solution CI (50×) (48:1:1) were added to incubate another 10 minutes, followed by 10 seconds sonication. The supernatant of the final spin was transferred into a third Eppendorf tube—this is membrane protein. Extracts were immediately stored at −20° C. until use.

B. Preparation of Total Protein Extract

Frozen tissues or cell pellets were weighed. 200 mg of each tissue was homogenized with a hand-held homogenizer and lysed in ice-cold 480 μl Solution TM, 10 μl Solution PI (50×) and 10 μl Solution CI (50×) (48:1:1). The resultant slurry was rocked gently at 4° C. for 30 minutes and was sonicated for 10 seconds before centrifugation for 10 minutes at 12000 rpm. The supernatant is then transferred into a fresh tube (total protein) for further analysis (gel electrophoresis and concentration measurement).

Verification of Compartmentalized Protein and Total Protein

A. Quantification of Protein for Yield Analysis of Compartmentalized Proteins and Total Protein DC Protein Assay (Cat. #500-0112, Bio-Rad Laboratories, 2000 Alfred Nobel Drive, Hercules, Calif. 94547) was used for protein concentration measurement according to kit instruction. BSA (Bovine Serum Albumin) was used as the standard. Yield of protein was calculated as percentage of wet weight of sample. Yield of proteins was also expressed as ratios between the different compartments.

B. Electrophoresis of Proteins for Analysis of Protein Band Patterns

10% or 5–10% gradient gel was used to analyze all protein samples in SDS-PAGE (SDS-polyacrylamide gel electrophoresis). 10 μg (for staining) or 40 μg (for Western Blotting) protein was loaded in each lane. Gels were either stained by Coomassie blue for analysis protein band patterns or transferred to membranes for Western analysis.

C. Western Blotting for Analysis of Compartment Specific Proteins

40 μg protein was loaded in each lane of a 5% or 10% or 5–20% gradient gel and transferred to PVDF (polyvinylidene difluoride) membrane (PVDF membrane can be used for sequential protein sequencing)(Cat. #162–0180, Bio-Rad, Hercules, Calif. 94547). The membrane was blocked with 5% non-fat milk in PBS-T (PBS with 0.5% Tween-20). Anti-β-actin mouse IgG (1:20000 dilution, Cat#A5441, Sigma, St. Louis, Mo.), anti-ERK1 goat IgG (1:200 dilution, Cat#sc-094-G, Santa Cruz Biotechnology, Santa Cruz, Calif.), Anti-EGFR goat IgG (1:200 dilution, Cat#sc-03-G, Santa Cruz Biotechnology, Santa Cruz, Calif.) and anti-SP1 mouse IgG (1:200 dilution, Cat#sc-420, Santa Cruz Biotechnology, Santa Cruz, Calif.) were used as primary antibodies. Anti-mouse IgG HRP conjugate (1:20000 dilution, Cat#NXA931, Amersham, N.J.) or anti-goat IgG HRP conjugate (1:10000, Cat#A5420, Sigma, St. Louis, Mo.) was used as secondary antibodies. ECL plus western blotting detection system (Cat#RPN2-132, Amersham, N.J.) was used for detection.

D. Ethidium Bromide Staining for Analysis of DNA Compartmentalization

The gels after protein SDS-PAGE and Coomassie blue staining were further stained by 0.5 μg/ml Ethidium Bromide for analysis of DNA compartmentalization (the indication if the nuclei were intact).

Optimization of Extraction Procedure

A. DNase Digestion of Protein Extract

DNase was add into protein extract in a concentration of 1–10 μg/ml, then incubated at room temperature for 30 min. to 2 hours, depending on the disappearance of stickiness caused by DNA.

B. Alteration of Concentration of NP-40

Concentration of NP-40 in extraction solutions was changed from 0% to 10% while other components were kept unchanged.

Confirmation of Protein Extraction

Appropriate separation or isolation of compartmentalized proteins from a sample of organisms, tissue, or cells was verified using four major assays. The yield of protein from each compartment was determined. Protein band pattern analysis of protein from each compartments was performed using SDS-PAGE. Western analysis of known compartment-specific proteins was performed. And, DNA location analysis was performed to confirm proper separation of the nuclear compartment from other compartments.

Results

Example 1

Separation and Isolation of Protein from Three Subcellular Compartments and Total Protein Extracted With the present invention, only a single experiment (or single sample) is needed for extracting proteins from cytoplasmic, nucleic and membrane compartments in the same container. From a single sample of human liver, cytoplasmic protein, nuclear protein or membrane protein were separated and isolated, as shown in FIG. 1. No significant amount of protein was found in the washes between extraction of the protein from the different subcellular compartments (see FIG. 9, panel A), and only insoluble cell/tissue debris remained at the completion of the extraction process. Therefore, the ratio among isolated protein from different subcellular compartments is kept the same as the natural ratio of protein among the compartments in whole tissues or cells, which is very important for gene expression study. This is different from isolation of protein from different compartments using as many different samples. Recovery rate of isolatable proteins is higher for the present procedure than for methods currently used because all processes are performed in the same container and no extra volume of reagent, no extra process steps such as precipitation, electrophoresis, chromatography, concentrating, dialysis, banding recovery, and no extra container or tubes for transferring are involved. As show in FIG. 1, proteins from cytoplasmic, nucleic or membrane compartments are well separated and recovered completely.

Figure 2:
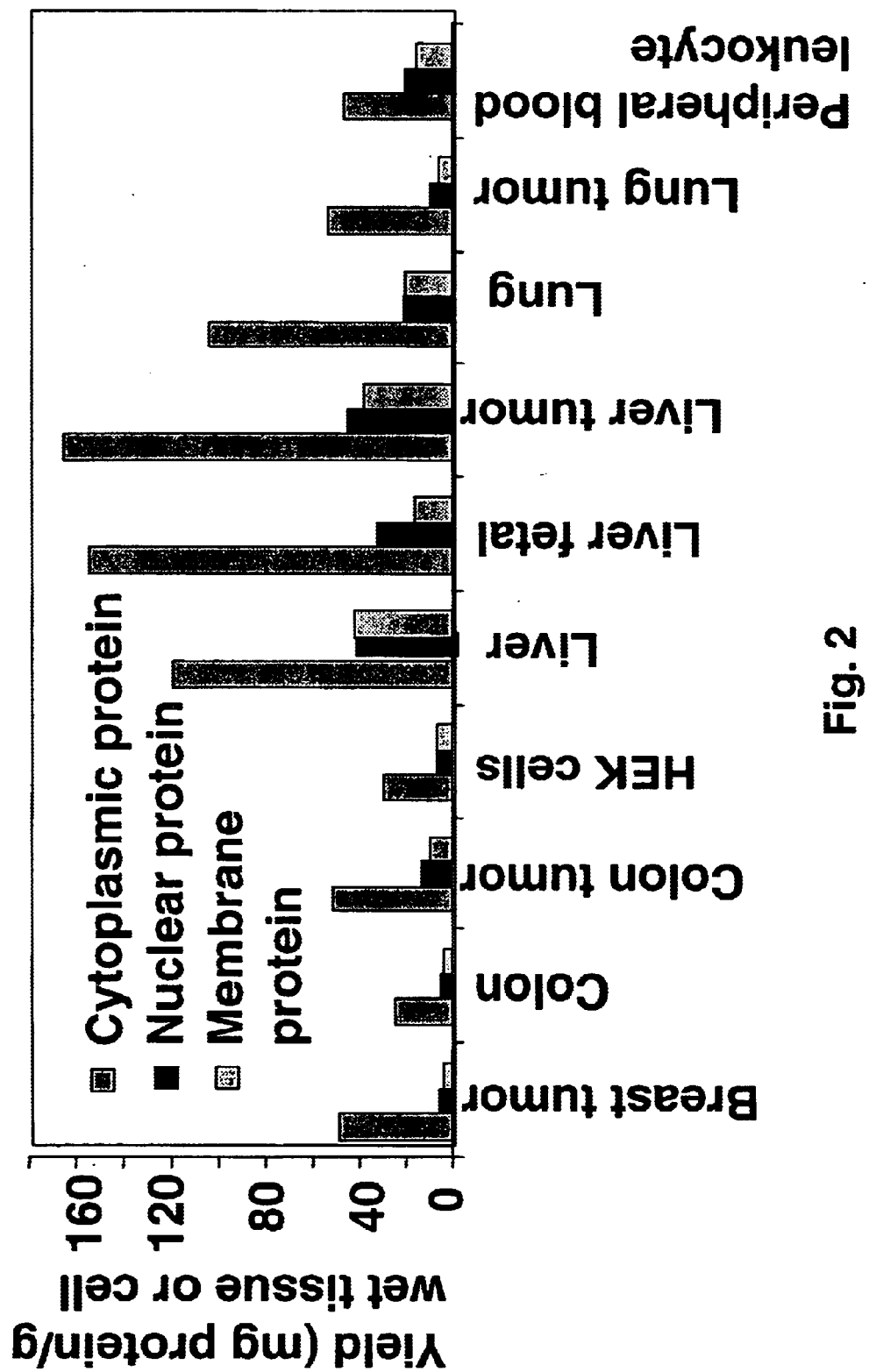
FIG. 2 shows the relative amounts of cytoplasmic protein, nuclear protein and membrane protein extracted from breast tumor tissue, normal colon tissue, colon tumor tissue, Human Embryo Kidney (HEK) cultured cells, normal liver tissue, fetal liver tissue, liver tumor tissue, normal lung tissue, lung tumor tissue, and peripheral blood leukocyte.

Similar experiments were performed for several other cell/tissue types, including breast tumor, colon, colon tumor, HEK cells, fetal liver, liver tumor, lung, lung tumor and peripheral blood leucocytes. FIG. 2 shows the relative amounts of protein extracted from each of the cytoplasmic, nuclear and membrane subcellular compartments. The yield ratio of cytoplasmic, nuclear and membrane protein is 5–10:1:1, which shows that the largest population of proteins is from the cytoplasmic compartment. However, the yields of compartmental protein vary from tissue to tissue. For example, only 6 mg of liver tissue produce 1 mg cytoplasmic protein, while extraction of 1mg cytoplasmic protein from colon requires 30 mg colon tissue. Generally, the cytoplasmic protein yield ranges from 70 to 80%, the nuclear or membrane protein yield is from 10 to 20%, of total protein.

Figure 3:
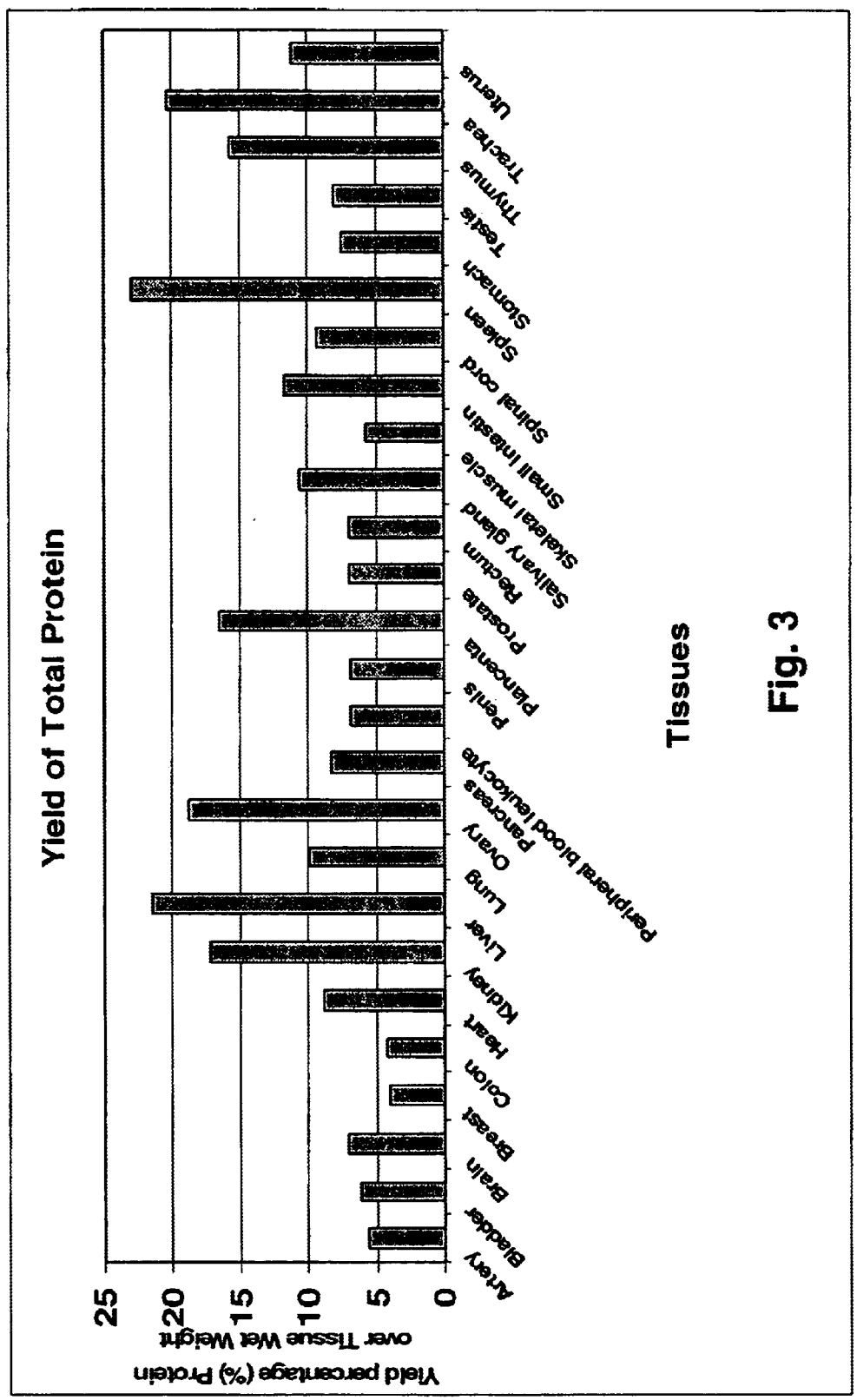
FIG. 3 shows total protein extracted from samples of artery, bladder, brain, breast, colon, heart, kidney, liver, lung, ovary, pancreas, peripheral blood leukocyte, penis, placenta, prostate, rectum, salivary gland, skeletal muscle, small intestine, spinal cord, spleen, stomach, testis, thymus, trachea, and uterus.

Total protein from artery, bladder, brain, breast, colon, heart, kidney, liver, lung, ovary, pancreas, peripheral blood leukocyte, penis, placenta, prostate, rectum, salivary gland, skeletal muscle, small intestine, spinal cord, spleen, stomach, testis, thymus, trachea, and uterus were extracted. The yield percentage of protein per weight of tissue sample is indicated in FIG. 3. The data show that the yield of proteins varied from tissue to tissue, ranging 4–25%. The average yield of total protein was about 10% of wet weight of tissue.

The yield ratio (5–10:1:1) of protein from the three identified subcellular compartments and yield of total protein (10%) are consistent with what is found in nature, confirming that the present invention is a reliable method to extract compartmentalized protein or total protein.

Example 2

Protein Band Pattern Analysis Among Protein from Different Compartments

Figure 4:
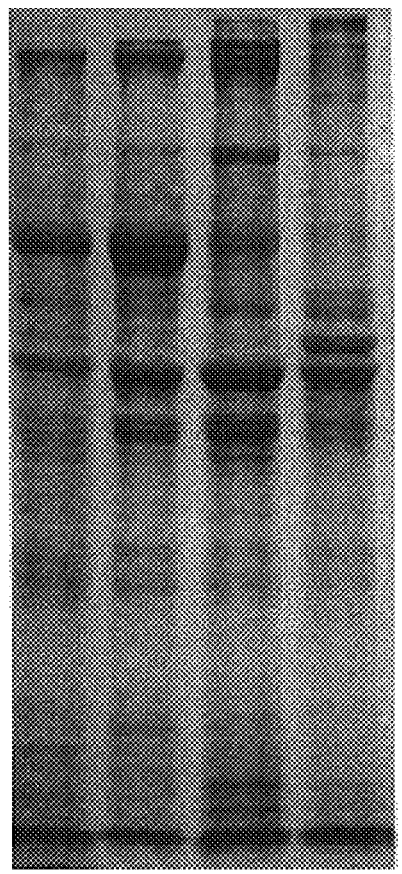
FIG. 4 shows SDS PolyAcrylamide Gel Electrophoresis (SDS-PAGE) of the protein extracted from human normal colon and breast tumor.
Figure 4:
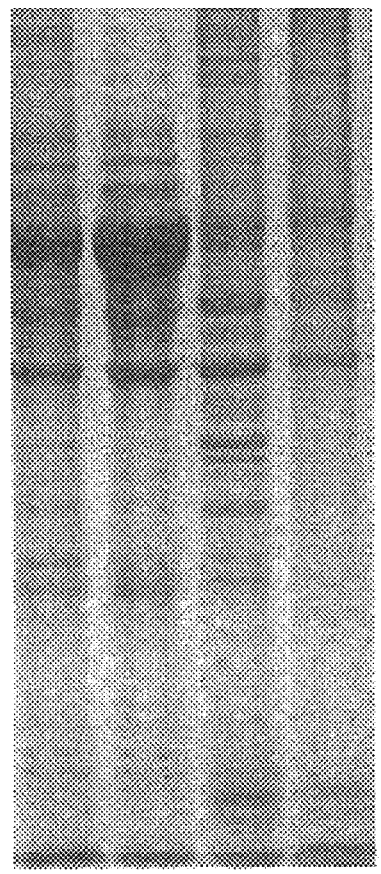

SDS PolyAcrylamide Gel Electrophoresis (SDS-PAGE) of the compartmentalized proteins extracted from human normal colon and breast tumor was performed using a 10% gel, stained by Coomassie blue. The results are shown in FIG. 4. 10 µg of sample was loaded in each lane. There was no protein carrying over between the different compartments, since wash was employed after each extracting step.

Data in FIG. 4 show that 1) Both in normal colon tissue and in breast tumor tissue, proteins extracted from different compartments showed different protein band patterns, i.e. the protein band pattern of cytoplasmic protein was different from that of nuclear protein or membrane protein; 2) Protein band patterns, as a set consisting of cytoplasmic, nuclear and membrane proteins, from normal Colon tissue was different from that from breast tumor tissue, i.e. the variation of protein band patterns among proteins from three subcellular compartments in one tissue was different from the protein band patterns among proteins from the same three subcellular compartments in another tissue.

Example 3

Western Blotting Analysis of Compartment-Specific Protein

A. Cytoplasmic Compartment-specific Protein

Figure 5:
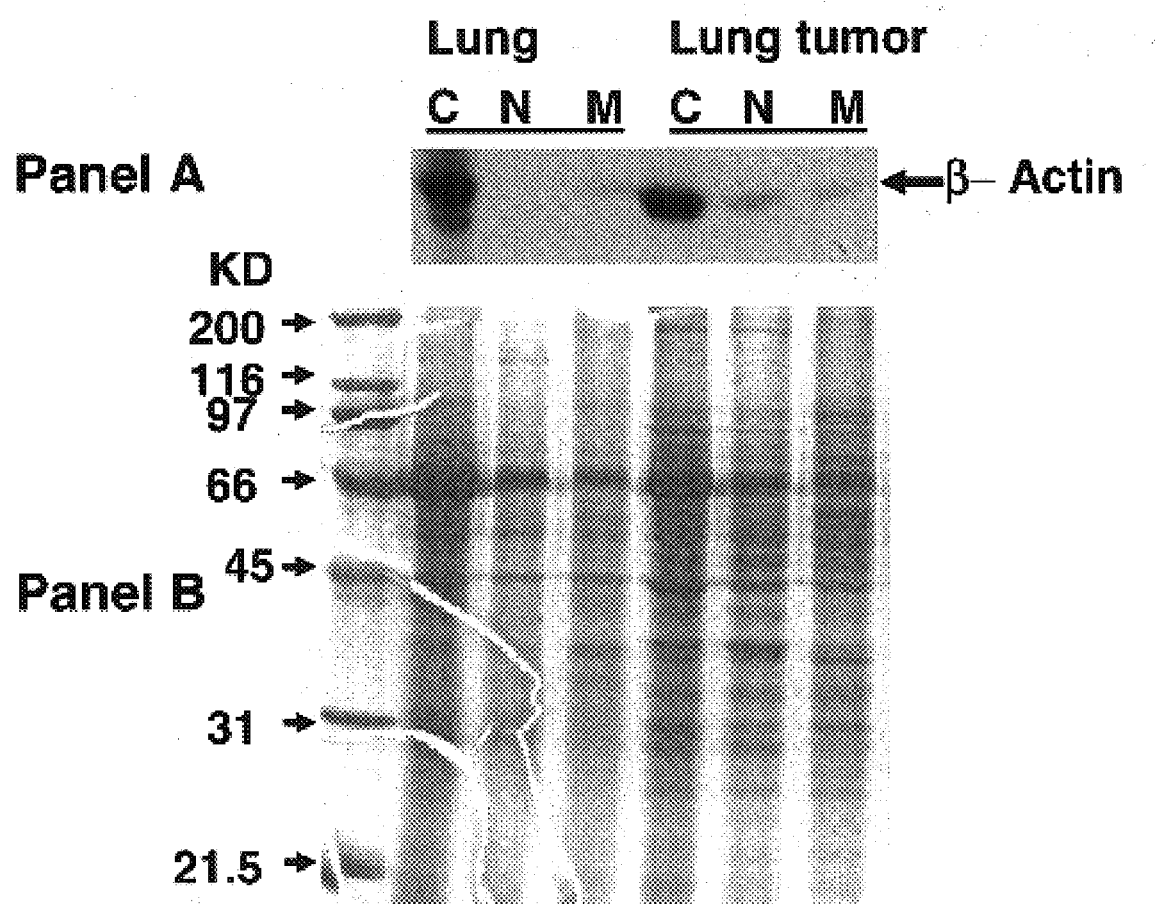
FIG. 5 shows analysis of cytoplasmic(C), nuclear (N) and membrane (M) protein extracted from normal lung and lung tumor tissues. Panel A: Anti-β-actin mouse monoclonal antibody was used to locate cytoplasmic protein in Western Blotting analysis. Panel B: SDS-PAGE of compartmentalized proteins from normal lung and lung tumor tissues, stained by Coomassie blue.

Cytoplasmic protein(C), nuclear (N) and membrane (M) proteins were extracted from normal lung and lung tumor tissues as shown in FIG. 5. Panel A: Anti-β-actin mouse monoclonal antibody was used to locate cytoplasmic protein in Western Blotting analysis. Panel B: SDS-PAGE of compartmentalized proteins from normal lung and lung tumor tissues, stained by Coomassie blue. Approximately 40 µg of each protein was loaded per lane.

the data show that Actin, as a cytoplasmic compartment specific protein, was specifically localized in the cytoplasmic portion (Lanes C) of extracted protein. There was only residue amounts of actin protein carrying over into the nuclear (Lanes N) and membrane (Lanes M) portions of extracted protein.

B. Nuclear Compartment-specific Protein

Figure 6:
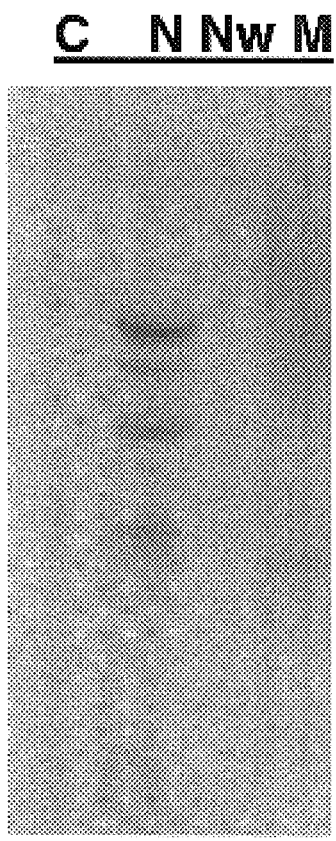
FIG. 6 shows analysis of cytoplasmic(C), nuclear(N), and membrane (M) protein extracted from cultured Human Embryo Kidney (HEK1) cells. Panel A: Anti-Sp1mouse monoclonal antibody was used to locate membrane protein Sp1 in Western Blotting analysis. Panel B: 5–20% gradient SDS-PAGE of compartmentalized protein from cultured HEK1 cells, stained by Coomassie blue.
Figure 6:
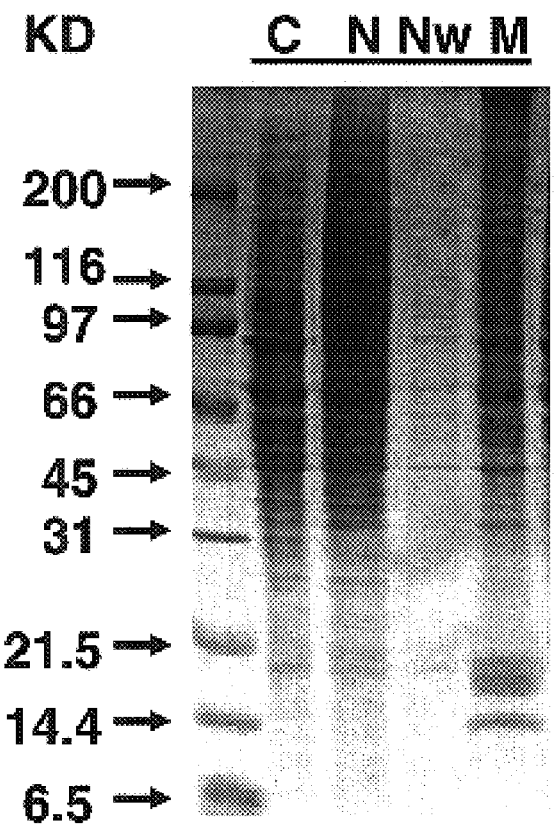

Cytoplasmic protein(C), nuclear protein (N), and membrane (M) proteins were extracted from culture HEK1 (Human Embryo Kidney) cells as shown in FIG. 6. Panel A: Anti-Sp1 mouse monoclonal antibody was used to locate membrane protein in Western Blotting analysis. Panel B: 5–20% gradient SDS-PAGE of compartmentalized protein from cultured HEK1 cells, stained by Coomassie blue. Approximately 40 µg of each protein was loaded per lane.

Data showed that Sp1 as a nuclear compartment specific protein was specifically localized in nuclear portion (Lanes N) of extracted protein. There was no Sp1 protein retained in the cytoplasmic portion (Lanes C) and no Sp1 protein left over in membrane portion (Lanes M) of extracted protein. There was no Sp1 protein left in the fraction of nuclear washing (Nw) between nuclear and membrane protein extraction.

C. Membrane Compartment-specific Protein

Figure 7:
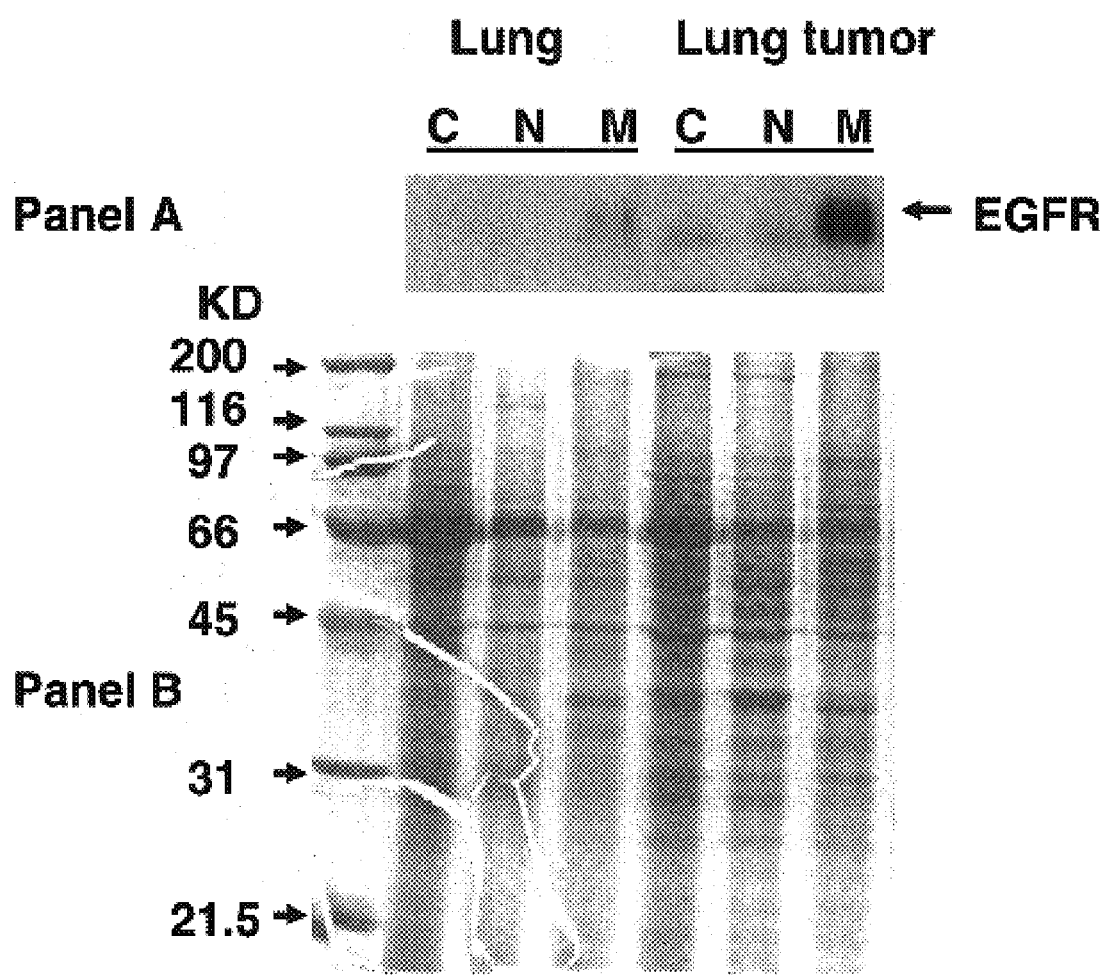
FIG. 7 shows analysis of cytoplasmic(C), nuclear (N) and membrane (M) protein extracted from normal lung and lung tumor tissues. Panel A: Anti-EGFR goat polyclonal antibody was used to locate membrane protein in Western Blotting analysis. Panel B: SDS-PAGE of protein from normal lung and lung tumor tissues, stained by Coomassie blue.

Cytoplasmic protein(C), nuclear (N) and membrane (M) proteins were extracted from normal lung and lung tumor tissues as shown in FIG. 7. Panel A: Anti-EGFR goat polyclonal antibody was used to locate membrane protein in Western Blotting analysis. Panel B: SDS-PAGE of compartmentalize protein from normal lung and lung tumor tissues, stained by Coomassie blue. Approximately 40 µg of each protein was loaded per lane.

The data show that EGFR, as a membrane compartment specific protein, was specifically localized in the membrane portion (Lanes M) of extracted protein. There was only residue amounts of EGFR protein retained in the nuclear (Lanes N) and cytoplasmic (Lanes C) portions of extracted protein. Lung tumor tissue expressed much more EGFR protein in membrane that normal lung tissue.

Figure 8:
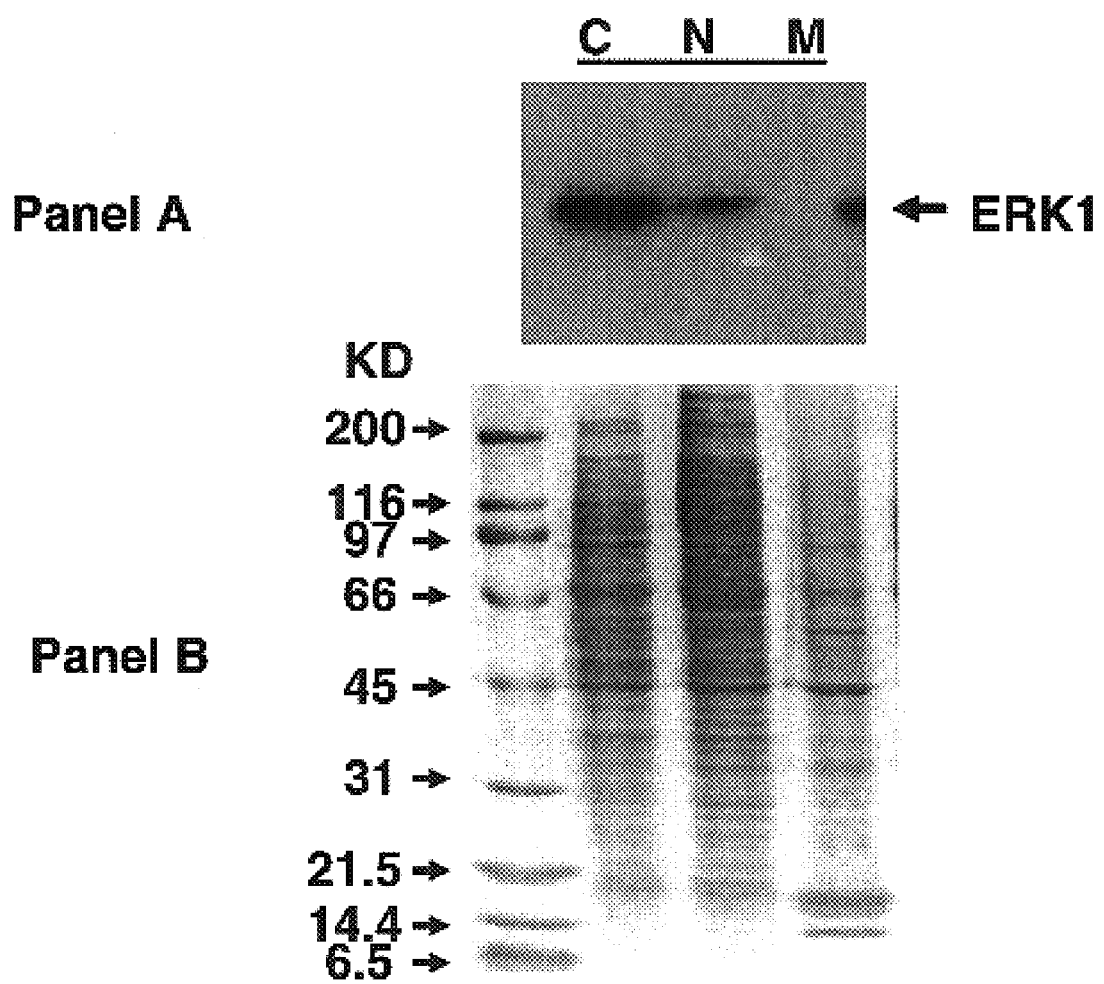
FIG. 8 shows analysis of cytoplasmic(C), nuclear (N) and membrane (M) protein extracted from cultured Human Embryo Kidney (HEK1) cells. Panel A: Anti-ERK1 polyclonal antibodies were used to locate ERK1 protein in Western Blotting analysis. Panel B: SDS-PAGE of compartmentalized proteins from cultured ERK1 cells, stained by Coomassie blue.

D. Identification of ERK1 Protein Compartmentalization in Cultured Human Embryo Kidney (HEK1) Cells by Western Blotting Cytoplasmic protein(C), nuclear (N) and membrane (M) proteins were extracted from cultured Human Embryo Kidney (HEK1) cells as shown in FIG. 8. Panel A: Anti-ERK1 polyclonal antibodies were used to locate ERK1 protein in Western Blotting analysis. Panel B: SDS-PAGE of compartmentalized proteins from cultured ERK1 cells, stained by Coomassie blue. Approximately 40 µg of each protein was loaded per lane.

The data show that the majority of ERK1 protein was located in the cytoplasmic compartment (Lanes C). There was a small amount of ERK1 protein located in the nuclear compartment (Lanes N) and no EKR1 protein located in the membrane compartment (Lanes M).

Example 4

DNA Staining Analysis of Nuclear DNA Compartmentalization as an Indicator of Nuclear Protein Compartmentalization Along with Western blotting data, DNA staining analysis of nuclear DNA compartmentalization in polyacrylamide gel indicates whether the nuclear membrane is intact or if nuclei were broken during extraction. DNA staining analysis directly monitors the status of nuclei or the location of nuclear content including DNA and protein during extraction of compartmentalized proteins.

Figure 9:
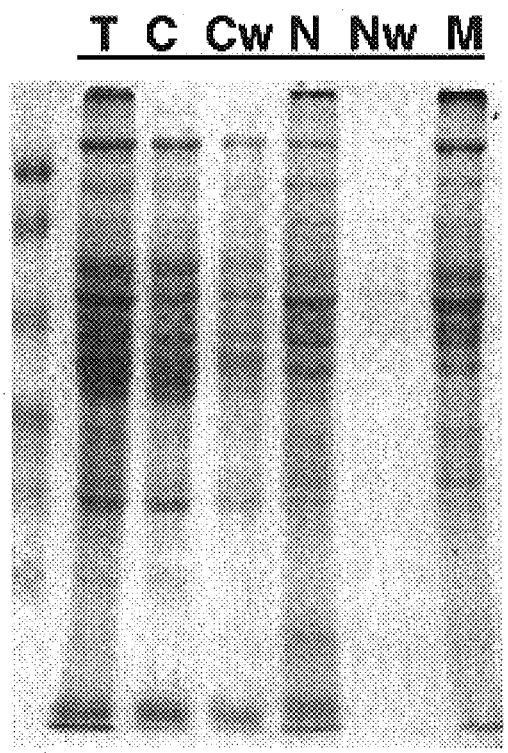
FIG. 9 shows analysis of total protein (T), cytoplasmic protein(C), nuclear protein (N) and membrane protein (M) extracted from human liver tissue, as well as of washes employed between cytoplasmic and nuclear protein extraction (Cw), and between nuclear extraction and membrane protein extraction (Nw). Panel A. Protein in 10% SDS PAGE gel was stained with Coomassie blue to show protein patterns. Panel B. The same gel was stained with Ethidium Bromide (EB) to show presence of DNA.
Figure 9:

Total protein (T), cytoplasmic protein(C), nuclear (N) and membrane (M) proteins were extracted from human liver tissue. Results are shown in FIG. 9. Washes were employed between cytoplasmic and nuclear protein extraction (Cw), and between nuclear extraction and membrane protein extraction (Nw). Panel A. Protein in 10% SDS PAGE gel was stained with Coomassie blue. 10 μg of protein was loaded in each lane. Panel B. The same gel was stained with Ethidium Bromide (EB).

The data show that nuclear DNA was localized in the fraction of nuclear protein extraction. There were only trace amount of DNA in the fraction of cytoplasmic protein extraction and membrane protein extraction. This indicated that nuclei were intact during the extraction of cytoplasmic protein. The nuclear protein portion of protein extract contained all the DNA and nuclear protein, and nuclear content was not present during extraction of membrane protein.

Example 5

Optimization of Procedures

A. Effect of DNase Digestion on Nuclear Protein Extraction

Figure 10:
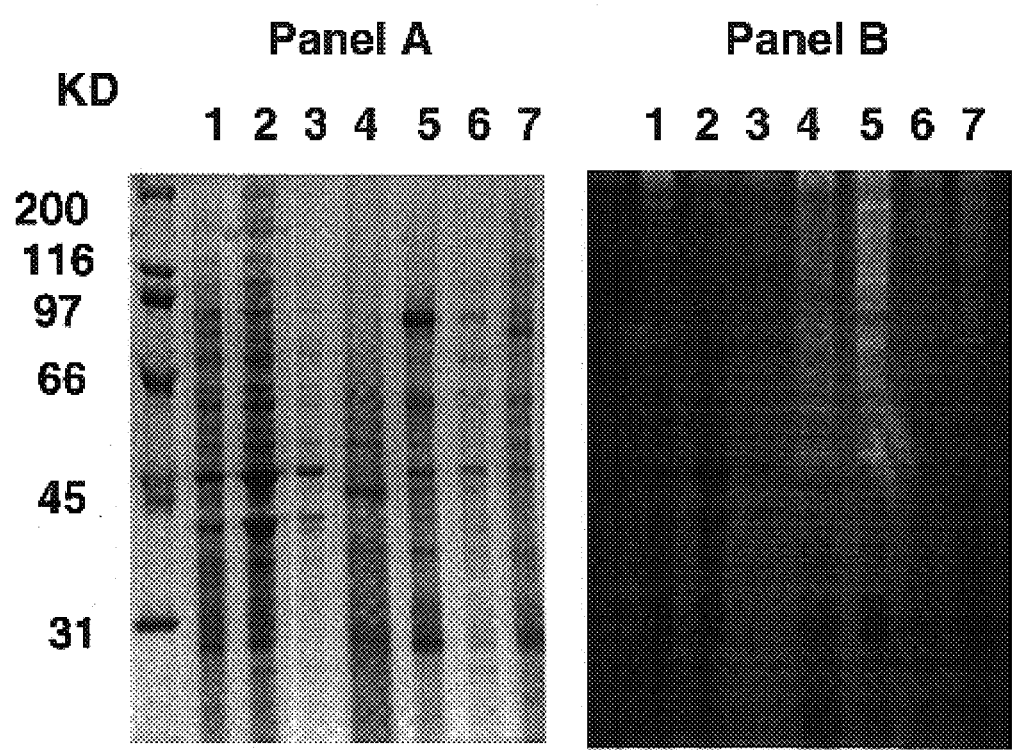
FIG. 10 shows the effect of DNase digestion on nuclear protein extraction. Total protein (lane 1), cytoplasmic protein (lane 2), nuclear protein (lanes 4 and 5) and membrane protein (lane 7) were extracted from human peripheral blood leukocytes. Lane 4 is nuclear protein extracted before DNase treatment and lane 5 is nuclear protein extracted after DNase treatment. Lane 3 is wash after cytoplasmic protein extraction and lane 6 is wash after nuclear protein extraction. Panel A. Protein in 10% SDS PAGE gel was stained with Coomassie blue. Panel B. The same gel was stained with Ethidium Bromide (EB).

During the development of this method, we also found that DNase treatment improves the extraction of nuclear protein. Total protein (lane 1), cytoplasmic protein (lane 2), nuclear (lane 4 and 5) protein and membrane (lane 7) proteins were extracted from human peripheral blood leukocytes. Results are shown in FIG. 10. Lane 4 is nuclear protein extracted before DNase treatment and lane 5 is nuclear protein extracted after DNase treatment. Lane 3 is wash after cytoplasmic protein extraction and lane 6 is wash after nuclear protein extraction. Panel A. Protein in 10% SDS PAGE gel was stained with Coomassie blue. 10 μg of protein was loaded in each lane. Panel B. The same gel was stained with Ethidium Bromide (EB).

The data show that DNASE treatment improved the yield and broadened the population of nuclear protein as indicated from lane 4 to lane 5 in Panel A. Meanwhile, more DNA was release after DNASE treatment as indicated from lane 4 to lane 5 in Panel B. Thus, DNASE digestion should be employed if DNA prevents isolation of nuclear or membrane proteins.

B. Effect of Surfactant on Membrane Protein Extraction

Figure 11:
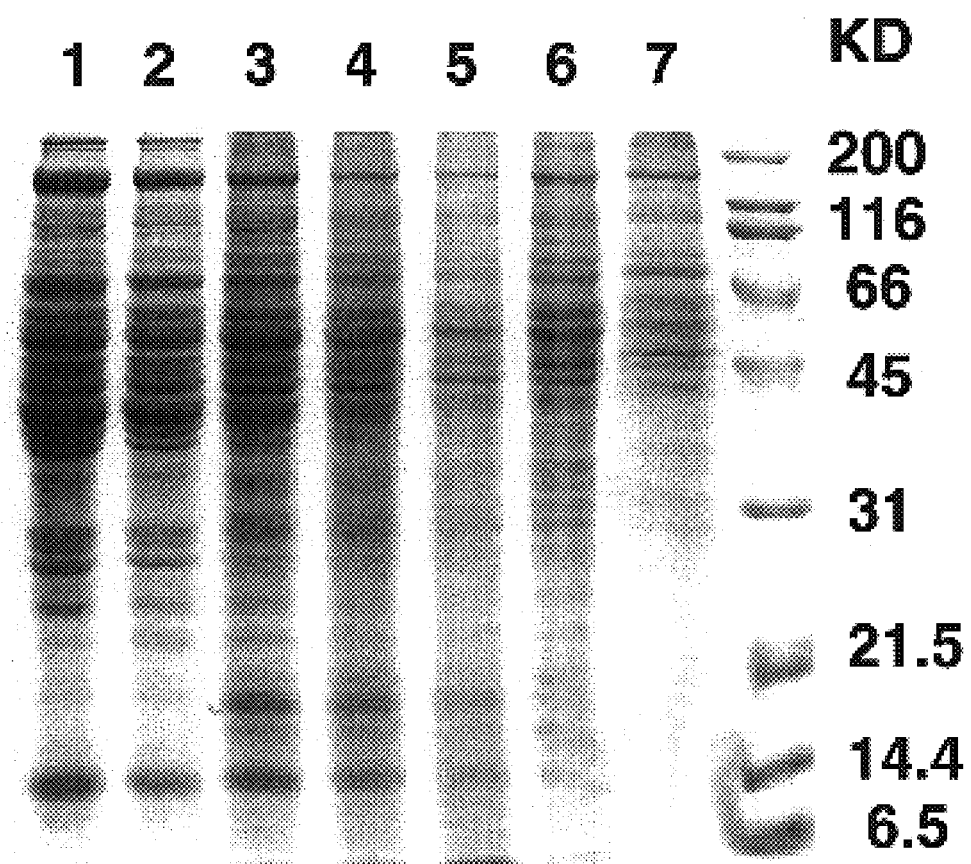
FIG. 11 shows the effect of surfactant on membrane protein extraction. Cytoplasmic protein (lane 1 and 2), nuclear protein (lane 3, 4 and 5) and membrane protein (lane 6 and 7) were extracted from human liver tissue. Lane 6 is membrane protein extracted with 1% NP-40 whereas lane 7 is membrane protein extracted with 0.5% NP-40. Protein in 10% SDS PAGE gel was stained with Coomassie blue. 10 μg of protein was loaded in each lane.

In addition, it was found that addition of 1% NP-40 gives a better yiel d and more diverse population of membrane protein than 0.5% NP-40. Cytoplasmic protein (lane 1 and 2), nuclear (lane 3, 4 and 5) protein and membrane (lane 6 and 7) proteins were extracted from human liver tissue. Results are shown in FIG. 11. Lane 6 is membrane protein extracted with 1% NP-40 whereas lane 7 is membrane protein extracted with 0.5% NP-40. Protein in 10% SDS PAGE gel was stained with Coomassie blue. 10 μg of protein was loaded in each lane.

The data show that the yield and population of membrane protein extracted with 0.5% NP-40 was significantly lower than that extracted with 1% NP-40. Therefore, the concentration of NP-40 was critical for extraction of membrane protein. Concentration of surfactant should be balanced between maximization membrane protein isolation and preservation of structure or activity of protein isolated. Adjust the volume of extraction solution to prevent saturation or over-dilution.

Example 6

Fingerprinting

A. Differentiating Normal Tissue Types

Figure 12:
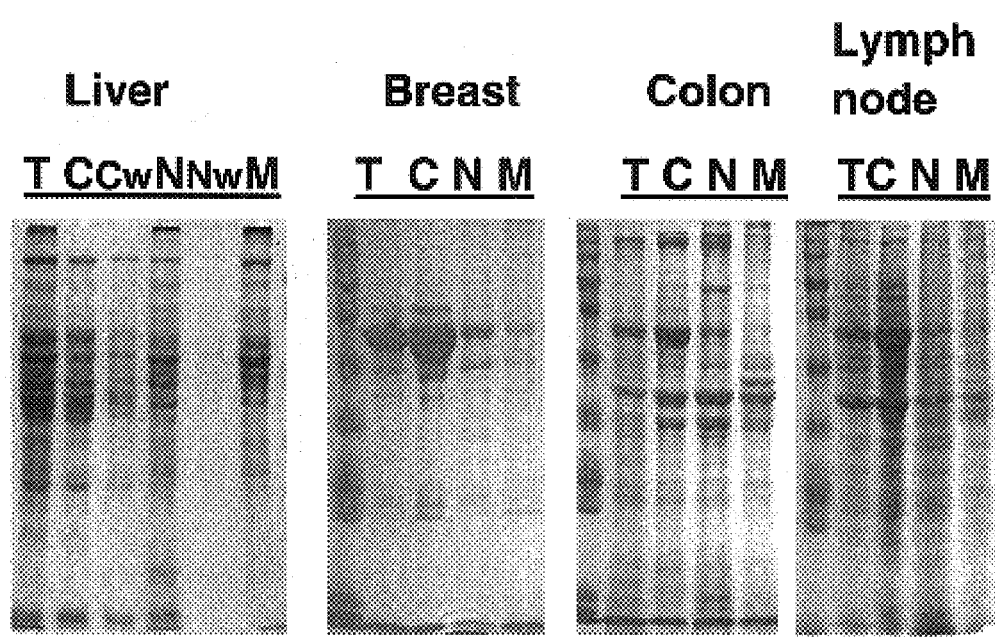
FIG. 12 shows the diversity of patterns of protein bands among different types of human normal tissues.

The present invention has been used to investigate various human tissues. Proteins from different compartments give different patterns on SDS-PAGE 10% gel. Proteins extracted from different normal tissues have their own distinguishing "finger print", as diversified protein band patterns among different types of normal tissues. Band patterns of proteins on SDS-PAGE from human liver, breast, colon and lymph node are shown in FIG. 12.

B. Differentiating Normal Tissue from Cancerous Tissue

Figure 13:
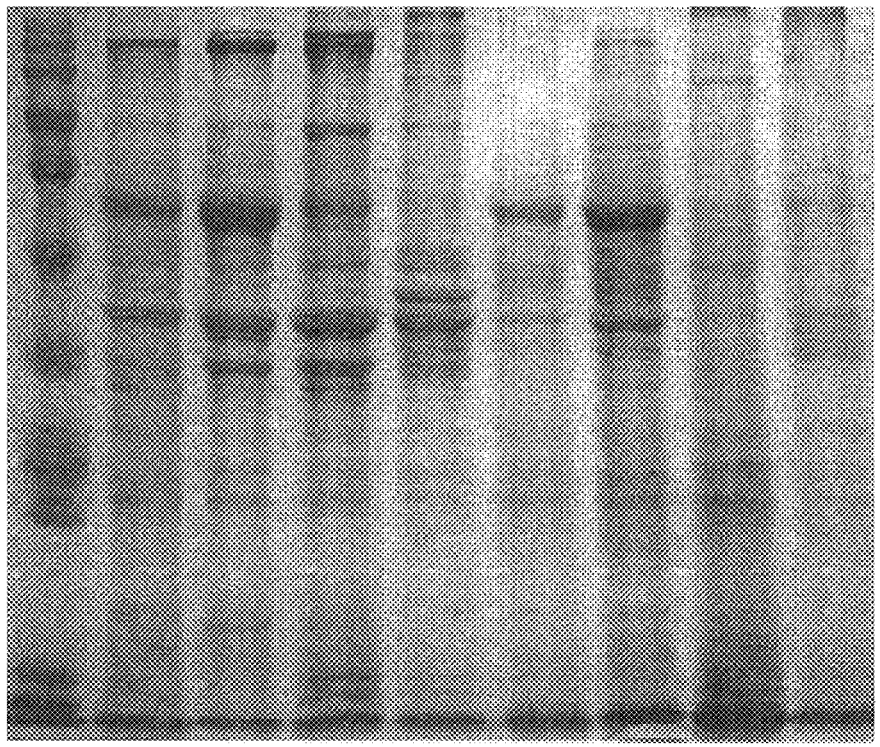
FIG. 13 shows the difference in protein band patterns between normal colon tissue and colon tumor tissue.
Figure 14:
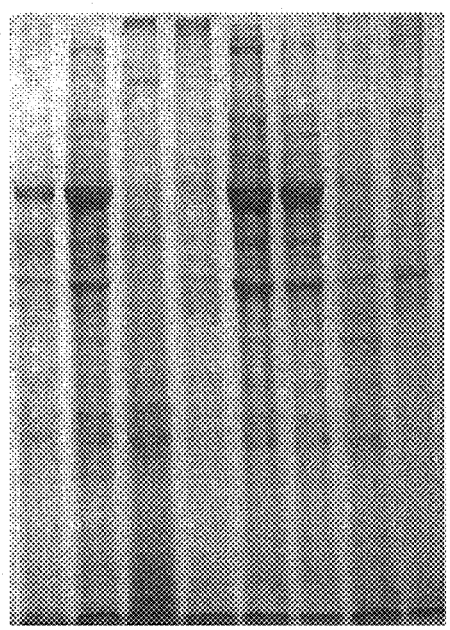
FIG. 14 shows the similarity of protein band patterns between primary tumor tissue and metastasis tumor tissue.
Figure 14:
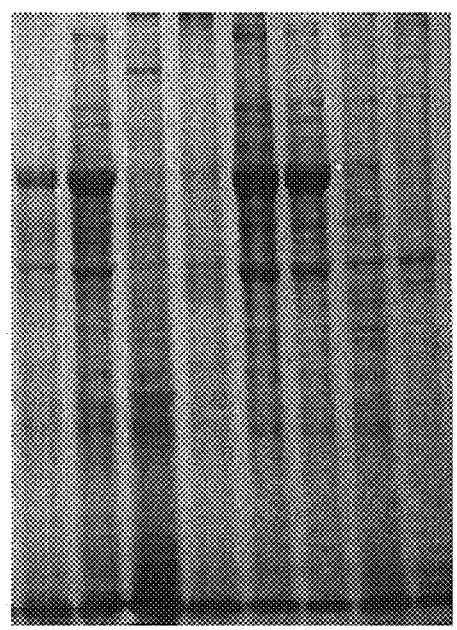

In a comparison of normal and tumor tissues, it was shown that protein band patterns from normal tissues were definitely different from that of tumor tissues. Data showed that pattern sets of protein bands of normal colon tissue was different from that from colon tumor tissue, dramatic differences were seen between the populations of two nuclear proteins (FIG. 13). However, the protein band patterns from primary tumors were similar to that of metastatic tumor tissue (FIG. 14). Furthermore, metastatic tumor tissues from different primary tumor showed similar protein band patterns to each other, and primary tumor tissues from different type of tissues showed similar protein band patterns to each other too (FIG. 14). As in normal tissue samples, proteins extracted from different compartments in tumor tissue showed different protein band patterns, i.e. the protein band pattern in cytoplasmic protein is different from that in nuclear protein or membrane protein.

The data show that pattern sets of protein bands of primary colon tumor tissue was similar to that of metastatic colon tumor tissue. In addition, pattern sets of protein bands of primary breast tumor tissue was similar to that from metastatic breast tumor tissue too. Furthermore, metastatic tumor tissues from different primary tumor showed similar protein band patterns to each other, and different tumors originating from different types of tissue showed relatively similar protein band patterns. Again, proteins extracted from different compartments showed different protein band patterns, i.e. protein band pattern in cytoplasmic protein were different from that in nuclear protein or membrane protein.

The present invention has discovered that tumor showed different protein band patterns from proteins band pattern showed by the same type of normal tissue. This means that tumor contains different protein population from protein population contained by normal tissues even though the tissue type is the same. On the contrary, primary tumor produced a similar protein band pattern to the protein band pattern produced by metastasis tumor originating from the same primary tumor. Furthermore, metastatic tumor tissues from different primary tumors showed the similar protein band patterns to each other, and different tumors originated from different type of tissues showed relatively similar protein band pattern, which indicates that different tumor may containing the similar protein population even though these tumors were originated from different types of normal tissue. Therefore, present discovery due to application of present invention concludes that all of the tumors originated from different types of normal tissue contain relatively similar protein population. This fact is matched with the fact that all of the tumors are in low differentiate status, thus contain less variety of proteins.

C. Differentiating Tissue of Different Developmental Stages

Figure 15:
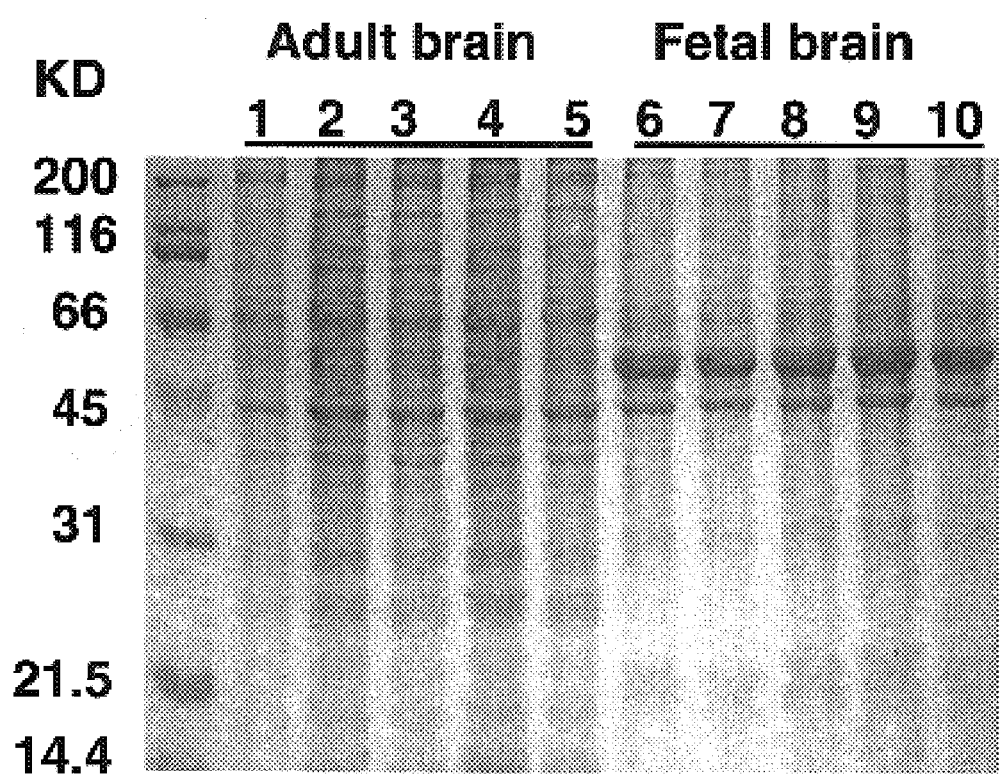
FIG. 15 shows the difference in protein band patterns in tissue of different development stages. Total proteins were extracted from adult brain tissues (lane 1–5) or fetal brain tissues (lane 6–10).

Tissues at different developmental stages contained different populations of protein. Total proteins were extracted from adult brain tissues (lane 1–5) or fetal brain tissues (lane 6–10) as shown in FIG. 15. Protein in 10% SDS PAGE gel was stained with Coomassie blue. 10 μg of protein was loaded in each lane.

Protein band patterns from fetal brain showed a very different pattern from that of adult brain. The fact that protein band patterns are different in fetus from the protein patterns in adult provides the clues to identify those proteins that play a significant role in development.

Figure 16:
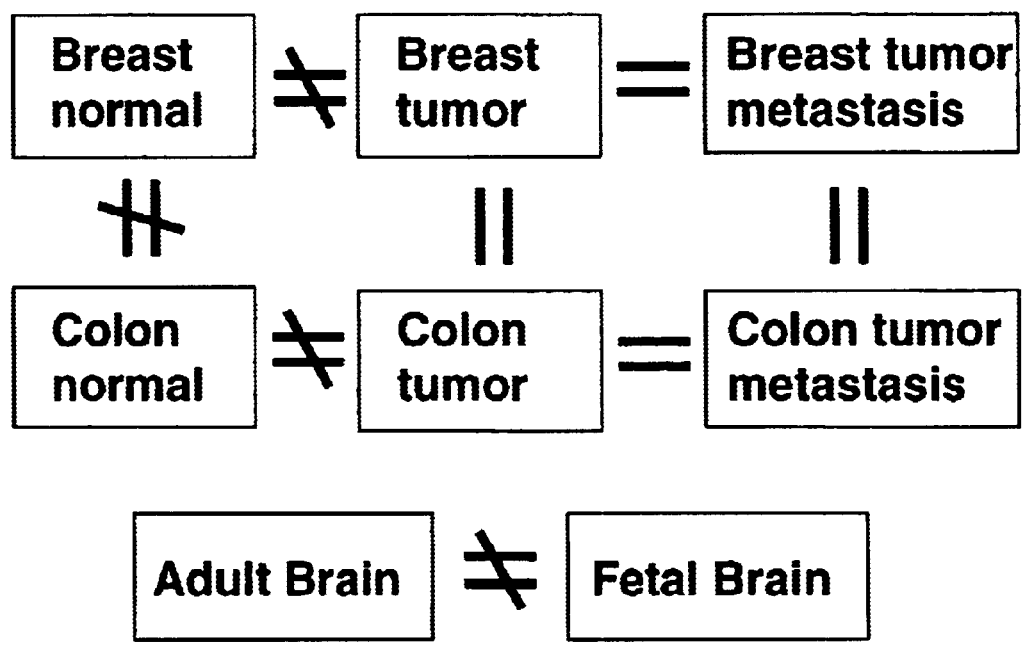
FIG. 16 summarizes the diversity or similarity of protein band patterns among different types of tissues. This application of the present invention reveals six phenomena.
  1. The protein band patterns are different from each other among different types of tissues.
  2. The protein band patterns of the same type of tissue are different from each other during different development stages.
  3. Normal tissues showed different protein band patterns from that of tumor tissues.
  4. Different types of tumor tissue showed similar protein band patterns among each other.
  5. Primary tumor tissues showed similar protein band patterns to metastatic tumor tissues.
  6. The metastatic tumor tissue from one type of primary tumor showed similar protein band patterns to metastatic tumor tissue from another type of primary tumor.

D. Discovery of Diversity or Similarity of Protein Band Patterns Among Different Types of Tissues As shown in FIG. 16, there are six phenomena being discovered by application of present invention.

1. The protein band patterns are different from each other among different types of tissues.
2. The protein band patterns of the same type of tissue are different from each other during different development stages.
3. Normal tissues showed different protein band pattern from that of tumor tissues.
4. Different types of tumor tissue showed the similar protein band patterns among each other.
5. Primary tumor tissues showed the similar protein band patterns as metastatic tumor tissues.
6. The metastatic tumor from one type of primary tumor showed the similar protein band patterns as the metastatic tumor from another type of primary tumor.

Example 7

Analysis of Protein Differential Display for Diagnosis and Treatment Development Identification of which compartments the status of proteins has changed between normal tissues and tumor tissues provides an indicator to focus on these suspicious proteins to develop diagnostic or treatment tools. For example, EGFR is over-expressed in the membrane compartment of protein from lung tumor tissue, as shown in FIG. 7. Then, these suspicious proteins can be transferred onto PVDF membrane and sequenced. With a partial sequence of the proteins, one can generate antibody and/or a nucleic acid probe to isolate and clone the gene encoding this protein. This principle can be employed to many other similar applications. Based on the fact that the different tissues have their own "finger prints", and the protein band patterns of normal tissue and tumor tissue are different, the protein pattern database can be established for diagnostic application. With a set of protein "finger prints", one can identify different tissues, diagnose tumor or metastasis, and design treatment programs.

What is claimed is:

1. A method of separating out protein from at least the cytoplasmic, nuclear and membrane fractions of a biological sample comprising cells, said method comprising:
   a) homogenizing a biological sample comprising cells in a cytoplasmic protein extraction solution;
   b) centrifuging said homogenate of step (a) forming a first supernatant and a first pellet;
   c) separating said first pellet from said first supernatant, said separated first supernatant forming a cytoplasmic protein fraction;
   d) suspending said separated first pellet from step(c) in a nuclear protein extraction solution;
   e) centrifuging said separated first pellet suspension from step (d) forming a second supernatant and a second pellet;
   f) separating said second supernatant from said second pellet from step (e) and said second separated supernatant forming the nuclear protein fraction;
   g) suspending said separated second pellet from step(f) in a membrane protein extraction solution;
   h) centrifuging said second pellet solution from step(g) forming a third supernatant and a third pellet;
   i) separating said third supernatant from said third pellet from step (h) forming the membrane protein fraction wherein each of the steps is performed on a single portion of the same initial biological sample comprising cells and all of said centrifugations and incubations is in the same container.

2. The method of claim 1, wherein said biological sample comprising cells is selected from the group consisting of a sample of organisms, a sample of tissue and a sample of cells.

3. The method of claim 1, wherein said cytoplasmic protein extraction solution is a low osmotic solution.

4. The method of claim 1, wherein said nuclear protein extraction solution is a high osmotic solution.

5. The method of claim 1, wherein said nuclear protein extraction solution comprises at least one DNase.

6. The method of claim 1, wherein said membrane protein extraction solution comprises at least one surfactant.

7. The method of claim 1, wherein one or more of said cytoplasmic protein extraction solution, nuclear protein extraction solution or membrane protein extraction solution comprises at least one protease inhibitor.

8. The method of claim 1, further comprising:
   j) measuring the amount of protein in each protein-containing supernatant, whereby the total protein per weight of sample and the relative distribution of protein in each subcellular compartment is determined.

9. A method of claim 1 further comprising:
   k) determining the presence of said protein(s) of interest in the protein isolated from each of said cytoplasmic, nuclear and membrane protein fractions, whereby the localization of said protein(s) of interest in one or more of said cytoplasmic, nuclear and membrane fractions is determined.

10. The method of claim 9, wherein step k is by one or more methods selected from the group consisting of gel band pattern analysis, antibody staining, Western Blot Analysis, ELISA, enzyme activity analysis, ligand binding analysis and receptor binding analysis.

* * * * *